US00PP21940P2

(12) United States Plant Patent
Tancredi

(10) Patent No.: US PP21,940 P2
(45) Date of Patent: May 31, 2011

(54) ***NANDINA* PLANT NAMED 'TUSCAN FLAME'**

(50) Latin Name: *Nandina domestica*
Varietal Denomination: Tuscan Flame

(76) Inventor: Robert John Tancredi, Salem, OR (US)

( * ) Notice: Subject to any disclaimer, the term of this patent is extended or adjusted under 35 U.S.C. 154(b) by 0 days.

(21) Appl. No.: 12/661,496

(22) Filed: Mar. 17, 2010

Related U.S. Application Data

(60) Provisional application No. 61/210,731, filed on Mar. 23, 2009.

(51) Int. Cl.
*A01H 5/00* (2006.01)

(52) U.S. Cl. ..... Plt./235

(58) Field of Classification Search ..... Plt./235
See application file for complete search history.

*Primary Examiner* — Annette H Para

(57) ABSTRACT

A new cultivar of *Nandina* plant named 'TUSCAN FLAME' that is distinguishable by compact bushy habit and year round bright red foliage that displays an overall lacy effect. In combination these traits set 'TUSCAN FLAME' apart from all other existing varieties of *Nandina* known to the inventor.

2 Drawing Sheets

Genus: *NANDINA*.
Species: *domestica*.
Denomination: 'TUSCAN FLAME'.

BACKGROUND OF THE INVENTION

This application claims the benefit of priority under 35 U.S.C. 119(e) of U.S. Provisional Patent application No. 61/210,731 filed on Mar. 23, 2009.

The present invention relates to a new and distinct cultivar of *NANDINA*, commonly known as heavenly bamboo, which is grown as an ornamental shrub for use in the garden and landscape. The new invention is known botanically as *NANDINA domestica* and will be referred to hereinafter by the cultivar name 'TUSCAN FLAME'. *NANDINA domestica* is in the family Berberidaceae.

'TUSCAN FLAME' was discovered in 2000 by the inventor as a vegetative branch sport which the inventor observed on an individual unnamed plant of the species *Nandina domestica* (unpatented). The parent plant was growing within a commercial crop of *Nandina domestica* at the inventor's nursery in Salem, Oreg.

'TUSCAN FLAME' is distinguishable from *Nandina domestica* by habit, foliage color, foliage appearance, and inflorescence size. The closest comparison plant known to the inventor is *Nandina* 'Moyer's Red' (unpatented). 'TUSCAN FLAME' is distinguishable from the comparison plant by habit and foliage color. In comparison with 'Moyer's Red', 'TUSCAN FLAME' is significantly more compact and bushy, standing less upright and retaining red foliage color year round.

'TUSCAN FLAME' grows with a bushy compact habit and requires little or no pruning. Foliage is finely divided resulting in an overall lacy effect, and topmost foliage color is bright red throughout the year, with underlying leaves that are yellow-green. 'TUSCAN FLAME' is best produced under part shade, and may be propagated using cuttings or tissue culture. Rooting is rapid and cuttings fill a 1-liter or 2-liter container in 9-12 months. Cultural requirements include full sun to partial shade, average water, and well-draining soil. The inflorescence of 'TUSCAN FLAME' is borne on second or third year old growth, and holds inconspicuous off-white flowers on short panicles that are tucked deep inside the foliage. 'TUSCAN FLAME' bears small red fruits which are generally obscured by the current season's foliage growth.

'TUSCAN FLAME' is suitable for use in gardens as a border plant, low hedge, container plant, or for use in the landscape where it is hardy in USDA Zone 6.

'TUSCAN FLAME' was first asexually propagated by the inventor in 2001 at the inventor's nursery in Salem Oreg. Asexual propagation was accomplished by taking basal stem cuttings. The inventor observed the original and the first (2001) propagated plants for a further seven years and has determined that the distinguishing characteristics of 'TUSCAN FLAME' are stable and uniform. Subsequent propagations have confirmed that 'TUSCAN FLAME' reproduces true to type in successive generations of asexual propagation.

SUMMARY OF THE INVENTION

The following traits have been repeatedly observed and represent the distinguishing characteristics of 'TUSCAN FLAME'. These traits in combination distinguish 'TUSCAN FLAME' from all other existing varieties of *Nandina* known to the inventor. 'TUSCAN FLAME' has not been tested under all possible conditions and phenotypic differences may be observed with variations in environmental, climatic, and cultural conditions, however, without any variance in genotype.

1. 'TUSCAN FLAME' grows with a compact bushy habit and requires little or no pruning.
2. The foliage of 'TUSCAN FLAME' is more finely divided than the species, resulting in an overall lacy effect.
3. 'TUSCAN FLAME' produces bright red foliage, which persists year round.
4. 'TUSCAN FLAME' is hardy in USDA Hardiness Zone 6.
5. 'TUSCAN FLAME' roots readily in 6-8 weeks and fills a 1-liter container in approximately 9 months.
6. The flowers of 'TUSCAN FLAME' are short relative to the species and are borne on second or third year old growth, and are generally obscured by the current season's growth.
7. The fruits of 'TUSCAN FLAME' are bright red and are generally obscured by the current season's growth.

BRIEF DESCRIPTION OF THE DRAWINGS

The accompanying color drawings illustrate the overall appearance of 'TUSCAN FLAME' showing the overall habit and the colors of its foliage and berries as true as is reasonably possible to obtain in color reproductions of this type. Color in the drawings may differ from color values cited in the detailed botanical description, which accurately describe the actual color of 'TUSCAN FLAME'.

The drawing labeled

The drawing labeled

Figure 1:
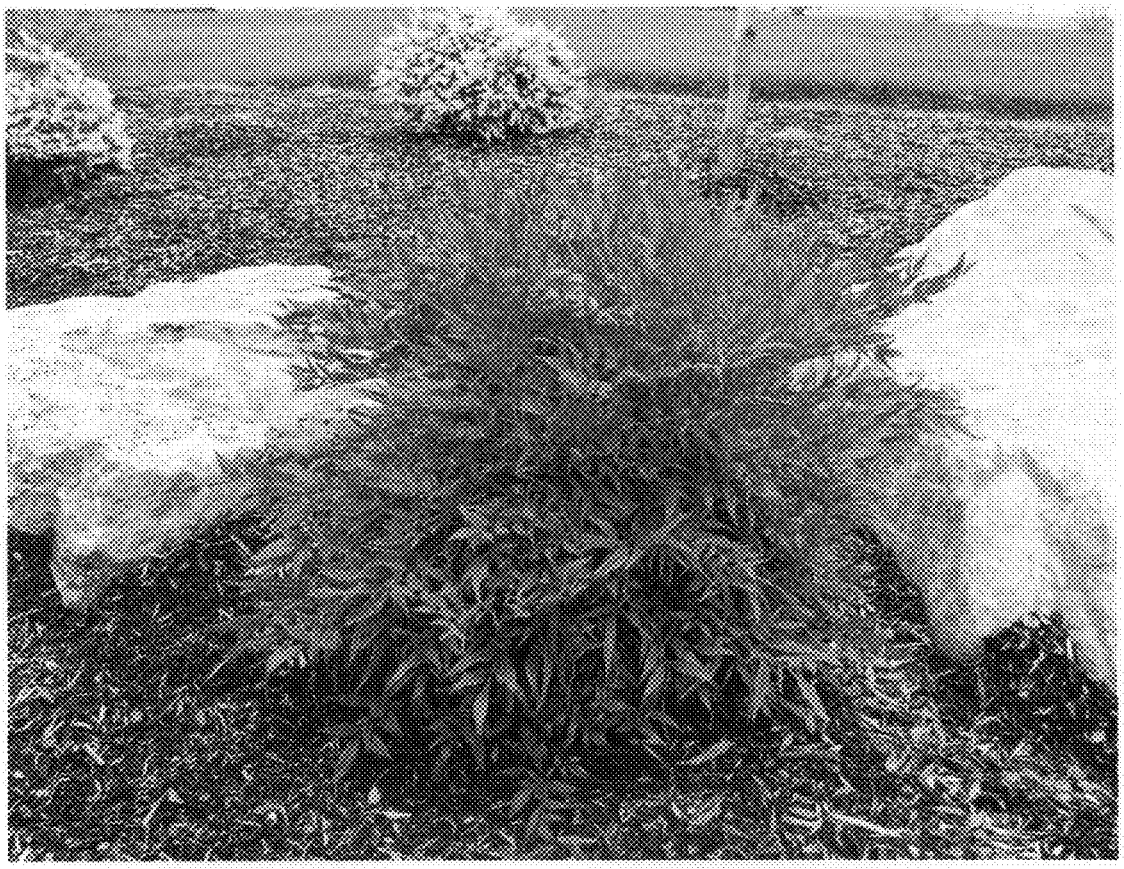
FIG. 1 shows a seven years old plant of 'TUSCAN FLAME' which has been established in the ground in Salem, Oreg. This drawing depicts the overall habit and bright red foliage color of 'TUSCAN FLAME'.
Figure 2:
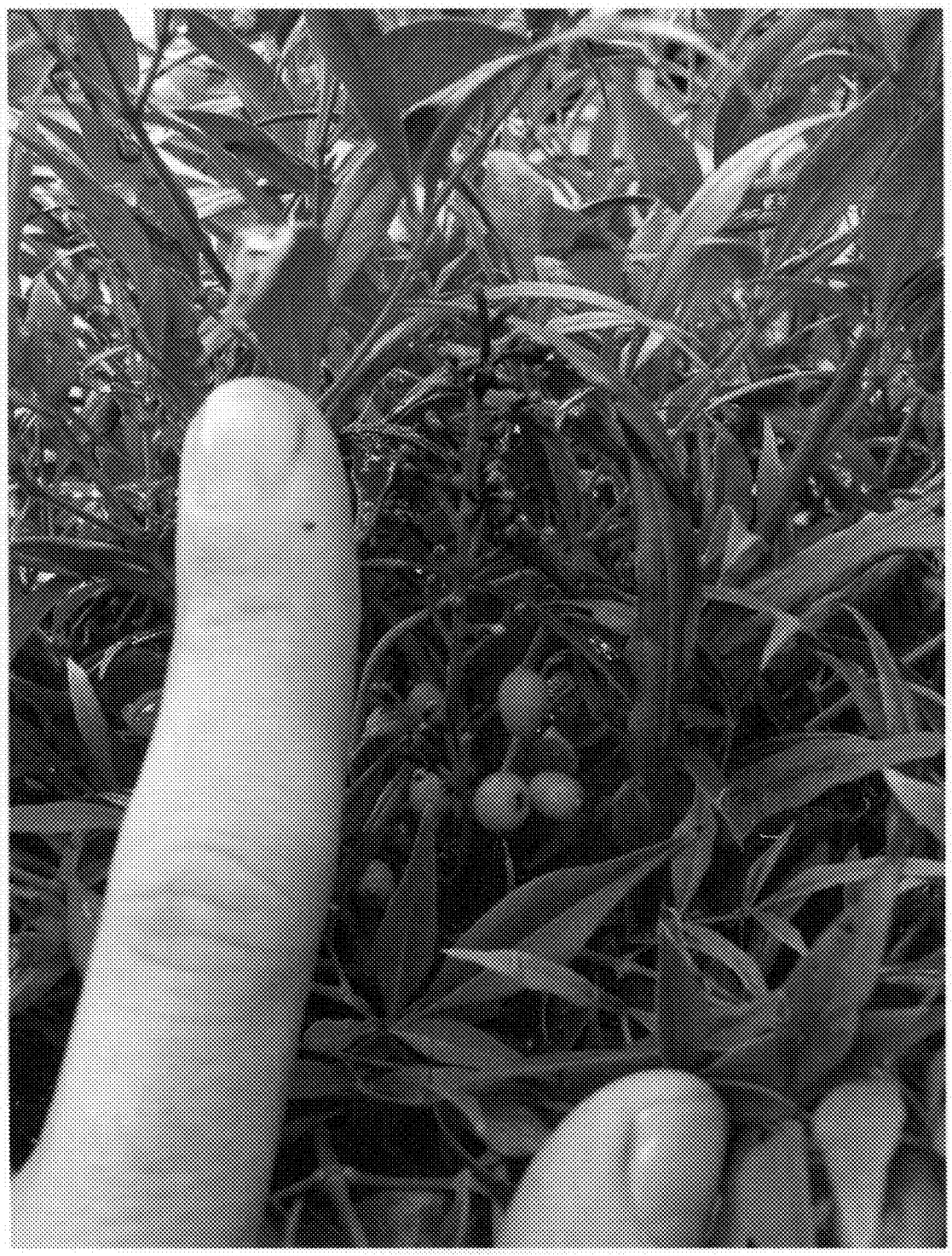
FIG. 2 shows a close-up view of the red fruits of 'TUSCAN FLAME'. The fruits are only visible when the foliage is parted as shown.

Both drawings were made using conventional techniques and although foliage colors may appear different from actual color due to light reflectance, they are as accurate as possible by conventional photography.

BOTANICAL DESCRIPTION OF THE PLANT

The following is a detailed botanical description of 'TUSCAN FLAME'. Color determinations are in accordance with 2001 The Royal Horticultural Society Colour Chart of London, England, except where general color terms of ordinary dictionary significance are used. The following observations, measurements and values were collected in March 2010 in Arroyo Grande, Calif., using a two and a half years old plant which had been grown out of doors in Salem, Oreg. immediately prior to shipment to California for the purposes of botanical data collection. Growing requirements are similar to the species.

Botanical classification: *NANDINA domestica* 'TUSCAN FLAME'.

Family: Berberidaceae.

Genus: *NANDINA*.

Species: *domestica*.

Denomination: 'TUSCAN FLAME'.

Common name: Heavenly Bamboo.

Commercial classification: Ornamental.

Use: Border plant, low hedge, or container plant in garden or in the landscape.

Parentage: *NANDINA domestica* 'TUSCAN FLAME' was discovered as a vegetative branch sport on an individual plant of the species *Nandina domestica*.

Pest and disease resistance: None known to the inventor.

Pest and disease susceptibility: None known to the inventor.

Plant description:

*Habit.*—Compact and bushy.

*Vigor.*—Vigorous.

*Type.*—Shrub.

*Height.*—35 cm.

*Width.*—52 cm.

*Root system.*—Thick and fibrous.

*Hardiness.*—USDA Zone 6.

*Propagation method.*—Vegetative stem cuttings.

*Time to develop roots* (*range*).—6-8 weeks to root cuttings.

*Crop time* (*average range*).—9-12 months to produce a 1-liter or 2-liter container plant.

*Cultural requirements.*—Grow in full sun to partial shade and well-draining soil, with average water.

*Stem.*—Trunk width: 1 cm. Trunk color: 177A. Trunk surface: Subcoriaceous. Mature stem width: 1 cm. Mature stem color: 183A. Mature stem surface: Subcoriaceous. Mature stem strength: Strong and rigid. Lateral stem length (average): 20 cm. Lateral stem diameter (average): 2 mm. Lateral stem surface: Longitudinally furrowed. Lateral stem shape: Closest to quadrangular. Lateral stem strength: Strong and flexible. Lateral stem color (range): 146C-146B. Internode (range): 5-8 cm. Node surface: Pubescent. Node color: 53B. Node dimensions: 5 mm in diameter and 3 mm. in height.

*Foliage.*—Type (range): Evergreen to semi-deciduous. Arrangement: Opposite. Leaf division: Compound. Leaf margin: Bipinnate. Quantity (average): 7 per lateral stem. Attachment (range): Petiolate to clasping. Leaf color (abaxial surface): Underlying leaves are in the yellow-green range 146A to 146C and top leaves remain in the red and purple range of 185A to 53A. Leaf color (adaxial surface): Underlying leaves are in the yellow-green range 146A to 146C and top leaves remain in the red and purple range of 185A to 53A. Leaf length (range): 6.0 cm-8.5 cm. Leaf width (range): 3.5 cm-6.0 cm. Leaf surface (abaxial): Glabrous. Leaf surface (adaxial): Glabrous. Pinnae shape (range): Oblanceolate to rhombic. Pinna margin: Entire. Pinna apex: Apiculate. Pinna base: Attenuate. Pinna color (abaxial surface): Underlying pinnae are in the yellow-green range 146A to 146C and top pinnae remain in the red and purple range of 185A to 53A. Pinna color (adaxial surface): Underlying pinnae are in the yellow-green range 146A to 146C and top pinnae remain in the red and purple range of 185A to 53A. Pinna length (range): 3.75 cm-5.0 cm. Pinna width (range): 1.10 cm-1.50 cm. Pinna surface (abaxial): Glabrous. Pinna surface (adaxial): Glabrous. Venation: Conspicuous depressed mid-vein. Vein color (abaxial surface): 183A. Vein color (adaxial surface): 183A. Petiolule length (range): 2 mm. to 1 cm. Petiolule diameter (average): <2 mm. Petiolule color: 187A. Petiolule surface: Glabrous. Fragrance: None observed.

Inflorescence:

*Type.*—Panicle.

*Length* (*range*).—7-10 cm.

*Width* (*average*).—4.5 cm.

*Peduncle color.*—185D.

*Peduncle length* (*range*).—7-10 cm.

*Flower quantity* (*average*).—30 per peduncle.

*Flower color.*—155A.

*Flower diameter.*—7.5 mm.

*Petals* (*range*).—3-6.

*Petal color.*—155A.

*Petal apex.*—Acute.

*Petal shape.*—Obovate.

*Petal length.*—5 mm.

*Petal width.*—3 mm.

*Lastingness* (*on the plant, range*).—1-3 days.

*Inflorescence appearance.*—Inconspicuous.

*Fragrance.*—Insignificant.

Reproductive organs:

*Stamens.*—6 in number.

*Color.*—13B.

*Pistil length.*—4 mm.

*Pistil width.*—1.5 mm.

*Pistil color.*—159D.

*Style color.*—159D.

*Stigma color.*—39A.
*Stigma shape.*—Conical.
*Ovary color.*—159D.
*Ovary diameter.*—<3 mm.
*Ovary.*—Superior.

Fruit:

*Color.*—N34B.
*Diameter.*—<1 cm.
*Shape.*—Ovoid.
*Surface.*—Glossy.

Seed: None observed to date.

The invention claimed is:

1. A new and distinct cultivar of *Nandina* plant named 'TUSCAN FLAME' as described and illustrated herein.

* * * * *